US009433689B2

(12) United States Patent
Hackel et al.

(10) Patent No.: US 9,433,689 B2
(45) Date of Patent: Sep. 6, 2016

(54) PROBES AND METHODS OF IMAGING NON-HODGKINS LYMPHOMA

(71) Applicant: The Board of Trustees of the Leland Stanford Junior University, Palo Alto, CA (US)

(72) Inventors: Benjamin Hackel, Edina, MN (US); Arutselvan Natarajan, Sunnyvale, CA (US); Sanjiv S. Gambhir, Portola Valley, CA (US)

(73) Assignee: The Board of Trustees of the Leland Stanford Junio, Palo Alto, CA (US)

( * ) Notice: Subject to any disclaimer, the term of this patent is extended or adjusted under 35 U.S.C. 154(b) by 101 days.

(21) Appl. No.: 14/204,039

(22) Filed: Mar. 11, 2014

(65) Prior Publication Data
US 2014/0271467 A1 Sep. 18, 2014

Related U.S. Application Data

(60) Provisional application No. 61/776,905, filed on Mar. 12, 2013.

(51) Int. Cl.
*A61K 49/00* (2006.01)
*A61K 51/08* (2006.01)

(52) U.S. Cl.
CPC .................................. *A61K 51/088* (2013.01)

(58) Field of Classification Search
CPC .... A61K 51/00; A61K 51/08; A61K 51/088; A61K 49/00; A61K 49/0004; A61K 2121/00; A61K 2123/00
USPC ...... 424/1.11, 1.65, 1.69, 1.81, 9.1, 9.2, 9.3, 424/9.4, 9.5, 9.6; 514/1, 1.1, 19.2, 19.3, 514/19.4, 19.5; 534/7, 10–14
See application file for complete search history.

(56) References Cited

U.S. PATENT DOCUMENTS

2014/0294765 A1* 10/2014 Cojocaru ............... C07K 16/28
424/85.2

OTHER PUBLICATIONS

Maloney DG. Immunotherapy for non-Hodgkin's lymphoma: monoclonal antibodies and vaccines. Journal of clinical oncology : official journal of the American Society of Clinical Oncology. 2005;23:6421-8.
Tedder TF, Engel P. CD20: a regulator of cell-cycle progression of B lymphocytes. Immunology today. 1994;15:450-4.
Tedder TF, Streuli M, Schlossman SF, Saito H. Isolation and structure of a cDNA encoding the B1 (CD20) cell-surface antigen of human B lymphocytes. Proceedings of the National Academy of Sciences of the United States of America. 1988;85:208-12.
Teeling JL, Mackus WJ, Wiegman LJ, van den Brakel JH, Beers SA, French RR, et al. The biological activity of human CD20 monoclonal antibodies is linked to unique epitopes on CD20. Journal of immunology. 2006;177:362-71.
Pagel JM, Hedin N, Subbiah K, Meyer D, Mallet R, Axworthy D, et al. Comparison of anti-CD20 and anti-CD45 antibodies for conventional and pretargeted radioimmunotherapy of B-cell lymphomas. Blood. 2003;101:2340-8.
Sharkey RM, Karacay H, Litwin S, Rossi EA, McBride WJ, Chang CH, et al. Improved therapeutic results by pretargeted radioimmunotherapy of non-Hodgkin's lymphoma with a new recombinant, trivalent, anti-CD20, bispecific antibody. Cancer Res. 2008;68:5282-90.
Miao Z, Ren G, Liu H, Jiang L, Cheng Z. Small-animal PET imaging of human epidermal growth factor receptor positive tumor with a 64Cu labeled affibody protein. Bioconjugate chemistry. 2010;21:947-54.
Nordberg E, Orlova A, Friedman M, Tolmachev V, Stahl S, Nilsson FY, et al. In vivo and in vitro uptake of 111 In, delivered with the affibody molecule (ZEGFR:955)2, in EGFR expressing tumour cells. Oncology reports. 2008;19:853-7.
Tolmachev V, Rosik D, Wallberg H, Sjoberg A, Sandstrom M, Hansson M, et al. Imaging of EGFR expression in murine xenografts using site-specifically labelled anti-EGFR 111In-DOTA-Z EGFR:2377 Affibody molecule: aspect of the injected tracer amount. European journal of nuclear medicine and molecular imaging. 2010;37:613-22.
Kimura RH, Cheng Z, Gambhir SS, Cochran JR. Engineered Knottin Peptides: A New Class of Agents for Imaging Integrin Expression in Living Subjects. Cancer Research. 2009;69:2435-42.
Gainkam LOT, Huang L, Caveliers V, Keyaerts M, Hernot S, Vaneycken I, et al. Comparison of the Biodistribution and Tumor Targeting of Two 99mTc-Labeled Anti-EGFR Nanobodies in Mice, Using Pinhole SPECT/Micro-CT. Journal of Nuclear Medicine. 2008;49:788-95.
Huang L, Gainkam LO, Caveliers V, Vanhove C, Keyaerts M, De Baetselier P, et al. SPECT imaging with 99mTc-labeled EGFR-specific nanobody for in vivo monitoring of EGFR expression. Molecular imaging and biology : MIB : the official publication of the Academy of Molecular Imaging. 2008;10:167-75.

(Continued)

*Primary Examiner* — D L Jones
(74) *Attorney, Agent, or Firm* — Thomas|Horstemeyer, LLP

(57) ABSTRACT

Embodiments of the present disclosure provide for labeled probes such as a $^{64}$Cu-FN3 probe (FN3 refers to fibronectin type 3 domain); methods of making labeled probes; pharmaceutical compositions including labeled probes; methods of using labeled probes; methods of diagnosing, localizing, monitoring, and/or assessing non-Hodgkin's lymphoma, cancers, tumors, precancerous cells, and related biological events using labeled probes; kits for diagnosing, localizing, monitoring, and/or assessing non-Hodgkin's lymphoma, cancers, tumors, precancerous cells, and related biological events; and the like.

19 Claims, 4 Drawing Sheets

(56) References Cited

OTHER PUBLICATIONS

Cai W, Chen K, He L, Cao Q, Koong A, Chen X. Quantitative PET of EGFR expression in xenograft-bearing mice using 64Cu-labeled cetuximab, a chimeric anti-EGFR monoclonal antibody. European journal of nuclear medicine and molecular imaging. 2007;34:850-8.

Niu G, Li Z, Xie J, Le Q-T, Chen X. PET of EGFR Antibody Distribution in Head and Neck Squamous Cell Carcinoma Models. Journal of Nuclear Medicine. 2009;50:1116-23.

Niu G, Sun X, Cao Q, Courter D, Koong A, Le Q-T, et al. Cetuximab-Based Immunotherapy and Radioimmunotherapy of Head and Neck Squamous Cell Carcinoma. Clinical Cancer Research. 2010;16:2095-105.

Sundaresan G, Yazaki PJ, Shively JE, Finn RD, Larson SM, Raubitschek AA, et al. 124I-Labeled Engineered Anti-CEA Minibodies and Diabodies Allow High-Contrast, Antigen-Specific Small-Animal PET Imaging of Xenografts in Athymic Mice. Journal of Nuclear Medicine. 2003;44:1962-9.

Lipovšek D. Adnectins: engineered target-binding protein therapeutics. Protein Engineering Design and Selection. 2011;24:3-9.

Koide A, Gilbreth RN, Esaki K, Tereshko V, Koide S. High-affinity single-domain binding proteins with a binary-code interface. Proceedings of the National Academy of Sciences. 2007;104:6632-7.

Hackel BJ, Kimura RH, Gambhir SS. Use of (64)Cu-labeled fibronectin domain with EGFR-overexpressing tumor xenograft: molecular imaging. Radiology. 2012;263:179-88.

Yuan F, Dellian M, Fukumura D, Leunig M, Berk DA, Torchilin VP, et al. Vascular Permeability in a Human Tumor Xenograft: Molecular Size Dependence and Cutoff Size. Cancer Research. 1995;55:3752-6.

Schmidt MM, Wittrup KD. A modeling analysis of the effects of molecular size and binding affinity on tumor targeting. Molecular Cancer Therapeutics. 2009;8:2861-71.

Zahnd C, Kawe M, Stumpp MT, de Pasquale C, Tamaskovic R, Nagy-Davidescu G, et al. Efficient Tumor Targeting with High-Affinity Designed Ankyrin Repeat Proteins: Effects of Affinity and Molecular Size. Cancer Research. 2010;70:1595-605.

Hackel BJ, Ackerman ME, Howland SW, Wittrup KD. Stability and CDR composition biases enrich binder functionality landscapes. Journal of molecular biology. 2010;401:84-96.

Koide A, Koide S. Monobodies: antibody mimics based on the scaffold of the fibronectin type III domain. Methods in molecular biology. 2007;352:95-109.

Tolcher AW, Sweeney CJ, Papadopoulos K, Patnaik A, Chiorean EG, Mita AC, et al. Phase I and pharmacokinetic study of CT-322 (BMS-844203), a targeted Adnectin inhibitor of VEGFR-2 based on a domain of human fibronectin. Clinical cancer research : an official journal of the American Association for Cancer Research. 2011;17:363-71.

Hackel BJ, Kapila A, Wittrup KD. Picomolar affinity fibronectin domains engineered utilizing loop length diversity, recursive mutagenesis, and loop shuffling. Journal of molecular biology. 2008;381:1238-52.

Chappell LL, Dadachova E, Milenic DE, Garmestani K, Wu C, Brechbiel MW. Synthesis, characterization, and evaluation of a novel bifunctional chelating agent for the lead isotopes 203Pb and 212Pb. Nuclear medicine and biology. 2000;27:93-100.

Natarajan A, Gowrishankar G, Nielsen CH, Wang S, Iagaru A, Goris ML, et al. Positron Emission Tomography of (64) Cu-DOTA-Rituximab in a Transgenic Mouse Model Expressing Human CD20 for Clinical Translation to Image NHL. Molecular imaging and biology : MIB : the official publication of the Academy of Molecular Imaging. 2012;14:608-16.

Lu SX, Takach EJ, Solomon M, Zhu Q, Law SJ, Hsieh FY. Mass spectral analyses of labile DOTA-NHS and heterogeneity determination of DOTA or DM1 conjugated anti-PSMA antibody for prostate cancer therapy. Journal of pharmaceutical sciences. 2005;94:788-97.

Gong Q, Ou Q, Ye S, Lee WP, Cornelius J, Diehl L, et al. Importance of cellular microenvironment and circulatory dynamics in B cell immunotherapy. Journal of immunology. 2005;174:817-26.

Natarajan A, Habte F, Gambhir SS. Development of a Novel Long-Lived ImmunoPET Tracer for Monitoring Lymphoma Therapy in a Humanized Transgenic Mouse Model. Bioconjugate chemistry. 2012.

Olafsen T, Betting D, Kenanova VE, Salazar FB, Clarke P, Said J, et al. Recombinant anti-CD20 antibody fragments for small-animal PET imaging of B-cell lymphomas. Journal of nuclear medicine : official publication, Society of Nuclear Medicine. 2009;50:1500-8.

Bakir MA, Eccles S, Babich JW, Aftab N, Styles J, Dean CJ, et al. c-erbB2 protein overexpression in breast cancer as a target for PET using iodine-124-labeled monoclonal antibodies. Journal of nuclear medicine : official publication, Society of Nuclear Medicine. 1992;33:2154-60.

Bloom L, Calabro V. FN3: a new protein scaffold reaches the clinic. Drug Discovery Today. 2009;14:949-55.

Pescovitz MD. Rituximab, an anti-cd20 monoclonal antibody: history and mechanism of action. American journal of transplantation : official journal of the American Society of Transplantation and the American Society of Transplant Surgeons. 2006;6:859-66.

Wadas TJ, Wong EH, Weisman GR, Anderson CJ. Copper chelation chemistry and its role in copper radiopharmaceuticals. Current pharmaceutical design. 2007;13:3-16.

Olafsen T, Sirk SJ, Betting DJ, Kenanova VE, Bauer KB, Ladno W, et al. ImmunoPET imaging of B-cell lymphoma using 124I-anti-CD20 scFv dimers (diabodies). Protein engineering, design & selection : PEDS. 2010;23:243-9.

\* cited by examiner

| FN3 clones (SEQ ID NO: of full sequence) | BC (aa of BC loop) | DE (aa of DE loop) | FG (aa of FG loop) | Framework |
|---|---|---|---|---|
| FN3WT (SEQ ID NO: 3) | DAPAVTVRY (aa 23-31 of SEQ ID NO: 3) | GSKST (aa 52-56 of SEQ ID NO: 3) | GRDGSPASSK (aa 77-86 of SEQ ID NO: 3) | |
| FN3$_{CD20}$ (SEQ ID NO: 2) | CRQRCADS (aa 25-32 of SEQ ID NO: 2) | GSWKT (aa 53-57 of SEQ ID NO: 2) | HYYGWDRYSH (aa 78-87 of SEQ ID NO: 2) | A74V |
| FN3$_{CD20-01}$ (SEQ ID NO: 4) | HYTCAGS (aa 25-31 of SEQ ID NO: 4) | GSWKT (aa 52-56 of SEQ ID NO: 4) | HYYGWDRYSH (aa 77-86 of SEQ ID NO: 4) | |
| FN3$_{CD20-02}$ (SEQ ID NO: 5) | HYTCADS (aa 25-31 of SEQ ID NO: 5) | WYVSN (aa 52-56 of SEQ ID NO: 5) | HYYGWDRYSH (aa 76-85 of SEQ ID NO: 5) | A74V |
| FN3$_{CD20-03}$ (SEQ ID NO: 6) | HSSDVSY (aa 25-31 of SEQ ID NO: 6) | YWFTN (aa 52-56 of SEQ ID NO: 6) | YRDCSSE (aa 77-83 of SEQ ID NO: 6) | E9G, A57T, V75A |

FIG. 1A

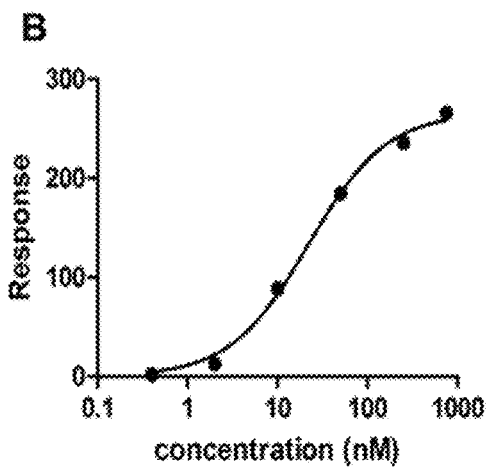

FIG. 1B

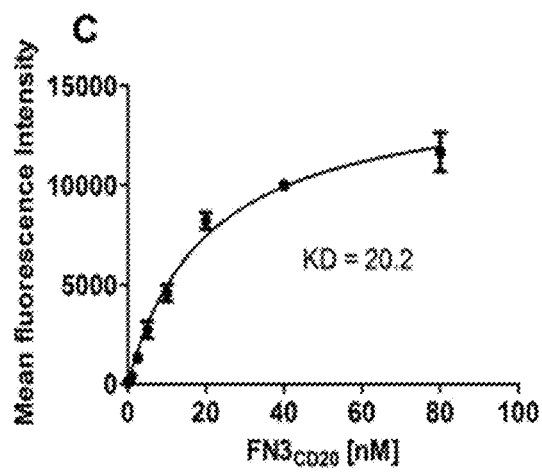

FIG. 1C

PROBES AND METHODS OF IMAGING NON-HODGKINS LYMPHOMA

CLAIM OF PRIORITY TO RELATED APPLICATION

This application claims priority to U.S. provisional application entitled "PROBES AND METHODS OF IMAGING NON-HODGKINS LYMPHOMA" having Ser. No. 61/776,905, filed on Mar. 12, 2013, which is entirely incorporated herein by reference.

SEQUENCE LISTING

The instant application contains a sequence listing which has been submitted with the instant application via EFS-Web. The sequence listing file is named 221907-1940_ST25.txt, is 6237 bytes in size, and is incorporated herein by reference in its entirety.

BACKGROUND

Methods of detecting and monitoring non-Hodgkin's lymphoma are important to the treatment of patients. Current technology is not ideally suited to detect and monitor non-Hodgkin's lymphoma. Thus, there is a need to overcome these deficiencies.

SUMMARY

Embodiments of the present disclosure provide for labeled probes such as a $^{64}$Cu-FN3 probe (FN3 refers to fibronectin type 3 domain); methods of making labeled probes; pharmaceutical compositions including labeled probes; methods of using labeled probes; methods of diagnosing, localizing, monitoring, and/or assessing non-Hodgkin's lymphoma, cancers, tumors, precancerous cells, and related biological events using labeled probes; kits for diagnosing, localizing, monitoring, and/or assessing non-Hodgkin's lymphoma, cancers, tumors, precancerous cells, and related biological events; and the like.

An embodiment of the present disclosure provides for a method of diagnosing the presence of a non-hodgkins lymphoma in a subject, and the method includes: administering to the subject a labeled probe with a sequence comprising a modified FN3 protein scaffold, wherein the probe binds to CD20 proteins; imaging at least a portion of the subject; and detecting the labeled probe, wherein the location of the labeled probe corresponds to the location of the non-Hodgkins lymphoma. In an embodiment, the labeled probe can include a sequence having SEQ ID NO: 2. In addition, the probe can include a metal such as: $^{64}$Cu, $^{89}$Zr, $^{86}$Y, or $^{68}$Ga, that is conjugated with the sequence.

An embodiment of the present disclosure includes a method of monitoring the progress of a non-Hodgkin's lymphoma in a subject, the method includes: administering to the subject a labeled probe with a sequence comprising a modified FN3 protein scaffold, wherein the probe binds to CD20 proteins; imaging at least a portion of the subject; and detecting the labeled probe, wherein the location of the labeled probe corresponds to the location of the non-Hodgkin's lymphoma, wherein the dimensions of the location are monitored over time.

An embodiment of the present disclosure includes a method of screening for an agent for treating a non-Hodgkin's lymphoma in a sample, the method includes: contacting the sample with a labeled probe with a sequence comprising a modified FN3 protein scaffold, wherein the probe binds to CD20 proteins, wherein a non-Hodgkin's lymphoma is present in the sample; contacting an agent with the sample; imaging at least a portion of the sample; and detecting the labeled probe, wherein the location of the labeled probe corresponds to non-Hodgkin's lymphoma, wherein the size of the location is monitored over time.

An embodiment of the present disclosure includes a probe that is a labeled probe, wherein the labeled probe includes a sequence having SEQ ID NO: 2.

An embodiment of the present disclosure includes a pharmaceutical composition including a pharmaceutical carrier and an effective dose of a labeled probe with a sequence comprising a modified FN3 protein scaffold, wherein the probe binds to CD20 proteins.

Other compositions, methods, features, and advantages will be, or become, apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE DRAWINGS

Many aspects of this disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1A is a table that illustrates the sequence alignment of FN3 variable domains. FN3$_{WT}$ (SEQ ID NO: 3), wild-type (WT), and FN3$_{CD20}$ (SEQ ID NO: 2) to FN3$_{CD20\text{-}03}$ (SEQ ID NOs: 4-6, respectively) clones listed in the table were selected against the CD20 peptide from the G4 library. Among the four unique clones, the clone (FN3$_{CD20}$) with the highest affinity and specificity was tested for in vitro live lymphoma cell binding assay using FACS. FN3$_{WT}$ (control) and FN3$_{CD20}$ (CD20 binder) were used for physico-chemical characterization and an in vivo animal imaging study. The sequences in the diversified BC, DE, and FG loops are presented as well as mutations within the framework that result from mutagenic PCR during evolution.

FIG. 1B illustrates a graph showing a Biacore 100 sensorgram analysis demonstrating that FN3$_{CD20}$ binds to CD20 peptide with nM affinity. Analysis shows the interaction between 15 µL of the 2-1500 nM FN3 proteins and the biotin-CD20 peptide coated on a sensor streptavidin chip (Biacore CM5 chip). FN3$_{CD20}$ protein (0.4, 2, 10, 50, 250, and 750 nM) was diluted in HBS and injected into the chip at a flow rate of 15 µL/min for 1 min at 25° C. The change in refractive index due to binding of FN3$_{CD20}$ and CD20 peptide was measured (response units) at these concentrations, and a 1:1 binding curve was fit, which yields a K$_D$ value of 22 nM.

FIG. 1C illustrates a graph showing the antigen-binding activity of FN3$_{CD20}$. Ramos cells were incubated with the indicated concentration (0.5-80 nM) of FITC-FN3$_{CD20}$ for 1 h at 4° C. Cells were washed and analyzed by flow cytometry. The data are expressed as the mean±standard deviation of three independent experiments. Data were normalized with respect to saturated fluorescence intensity (plateau) observed at the highest target concentrations. A 1:1 binding curve fit to the data indicates K$_D$=20 nM.

DETAILED DESCRIPTION

Figure 2:
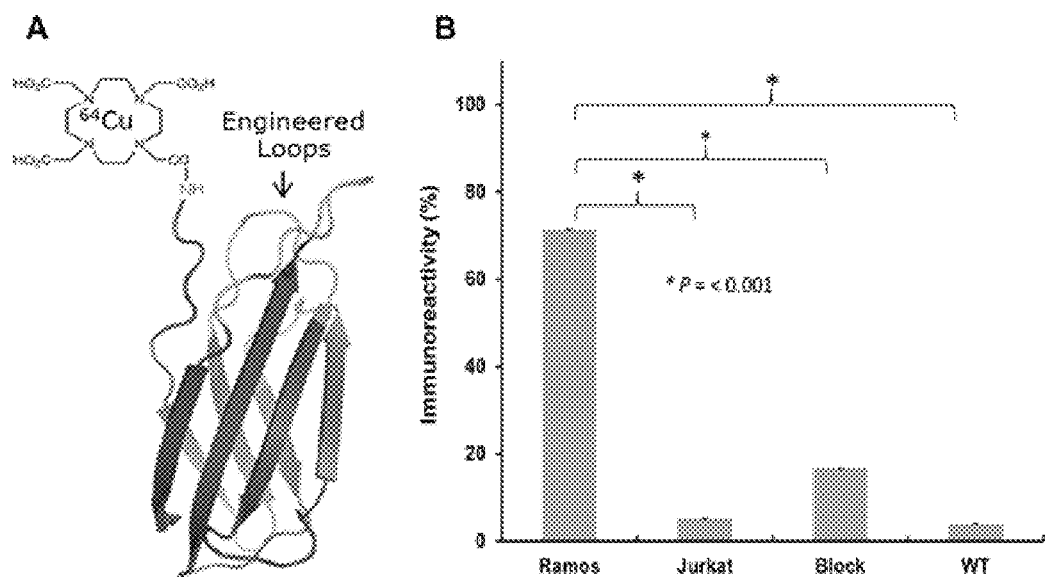
FIG. 2A illustrates a schematic diagram of $^{64}$Cu-Do-FN3 (FN3 domain depicted as the NMR solution structure of wild-type fibronectin domain (PDB code: 1TTG)). Mutated residues for CD20 binding shown engineered loops.
FIG. 2B illustrates a graph of a $^{64}$Cu-Do-FN3$_{CD20}$ tracer that exhibits specific binding on B cells. Ramos: CD20-positive; Jurkat: CD20-negative; Block: Ramos cells blocked with 1000 nM of unlabeled FN3$_{CD20}$ 0.5 h prior to $^{64}$Cu-FN3$_{CD20}$ tracer addition; WT: Ramos cells labeled with nonbinding control $^{64}$Cu-FN3$_{WT}$. Value and error bars represent the mean and standard deviation of triplicate samples.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

By "administration" or "administering" is meant introducing a probe or a labeled probe (also referred to as the "imaging agent") of the present disclosure into a subject. The preferred route of administration of the compounds is intravenous. However, any route of administration, such as oral, topical, subcutaneous, peritoneal, intra-arterial, inhalation, vaginal, rectal, nasal, introduction into the cerebrospinal fluid, or instillation into body compartments can be used.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties (e.g., binding to the CD20 antigen). A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A variant of a polypeptide includes conservatively modified variants. A substituted or inserted amino acid residue may or may not be one encoded by the genetic code. A variant of a polypeptide may be naturally occurring, such as an allelic variant, or it may be a variant that is not known to occur naturally.

Modifications and changes can be made in the structure of the polypeptides of this disclosure and still obtain a molecule having similar characteristics (e.g., biological properties such as binding to the CD20 antigen) as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest as long as they retain the characteristics of the primary sequence described herein.

"Identity," as known in the art, is a relationship between two or more polypeptide sequences, as determined by comparing the sequences. In the art, "identity" also means the degree of sequence relatedness between polypeptides as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present disclosure.

By way of example, a polypeptide sequence may be identical to the reference sequence, that is 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

Conservative amino acid variants can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxy-ethylcysteine, hydroxyethylhomocysteine, nitro-glutamine, homoglutamine, pipecolic acid, thiazolidine carboxylic acid, dehydroproline, 3- and 4-methylproline, 3,3-dimethylproline, tert-leucine, norvaline, 2-azaphenyl-alanine, 3-azaphenylalanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an E. coli S30 extract and commercially available enzymes and other reagents. Proteins are purified by chromatography. (Robertson, et al., J. Am. Chem. Soc., 113: 2722, 1991; Ellman, et al., Methods Enzymol., 202: 301, 1991; Chung, et al., Science, 259: 806-9, 1993; and Chung, et al., Proc. Natl. Acad. Sci. USA, 90: 10145-9, 1993). In a second method, translation is carried out in Xenopus oocytes by microinjection of mutated mRNA and chemically aminoacylated suppressor tRNAs (Turcatti, et al., J. Biol. Chem., 271: 19991-8, 1996). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. (Koide, et al., Biochem., 33: 7470-6, 1994). Naturally occurring amino acid residues can be converted to non-naturally occurring species by in vitro chemical modification. Chemical modification can be combined with site-directed mutagenesis to further expand the range of substitutions (Wynn, et al., Protein Sci., 2: 395-403, 1993).

As used herein the term "isolated" is meant to describe a polypeptide that is in an environment different from that in which the polypeptide naturally occurs, if it naturally occurs.

In accordance with the present disclosure, "a detectably effective amount" of the probe of the present disclosure is defined as an amount sufficient to yield an acceptable image using equipment that is available for clinical use. A detectably effective amount of the probe of the present disclosure may be administered in more than one injection. The detectably effective amount of the probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "host" or "subject" includes vertebrates such as humans and mammals (e.g., cats, dogs, horses, etc.). Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living subject" refers to a subject noted above that is alive and is not dead. The term "living subject" refers to the entire subject and not just a part excised (e.g., a liver or other organ) from the living subject.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue.

The term "detectable" refers to the ability to detect a signal over the background signal.

The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

In an embodiment, cancer refers to non-Hodgkin's lymphoma.

General Discussion

Embodiments of the present disclosure provide for labeled probes such as a $^{64}$Cu-FN3 probe (FN3 refers to fibronectin type 3 domain); methods of making labeled probes; pharmaceutical compositions including labeled probes; methods of using labeled probes; methods of diagnosing, localizing, monitoring, and/or assessing non-Hodgkin's lymphoma, cancers, tumors, precancerous cells, and related biological events using labeled probes; kits for diagnosing, localizing, monitoring, and/or assessing non-Hodgkin's lymphoma, cancers, tumors, precancerous cells, and related biological events; and the like. In particular, the present disclosure includes methods relating to non-invasive imaging (e.g., using a positron emission tomography (PET) imaging system) using labeled probes, such as a $^{64}$Cu-FN3 probe, in vivo. Additional details are described in the Examples.

Portions of the present disclosure discuss labeled probes while other portions describe a specific embodiment of the labeled probes, the $^{64}$Cu-FN3 probe. Discussions focusing on the $^{64}$Cu-FN3 probe are not limiting to the scope of the disclosure, rather those discussions are merely describing an exemplary embodiment of the present disclosure.

Embodiments of the present disclosure are advantageous for at least the following reasons. In an embodiment, the labeled probe clears fast from the blood and can achieve a high target organ-to-blood ratio within about 2 to 4 hours (e.g., a spleen-to-blood ratio of about 3 in about 4 hours). In addition, embodiments of the labeled probe are stable at room temperature and are soluble in organic and aqueous solvents. Furthermore, embodiments of the present disclosure are easy to produce in multi-gram quantities, at room temperature, at a relatively low cost.

Embodiments of the present disclosure include methods for imaging a sample (e.g., tissue or cell(s)) or a subject, that includes contacting a sample with or administering to a subject a labeled probe (e.g., $^{64}$Cu-FN3 probe) and imaging the sample with a PET imaging system. The imaging can be performed in vivo and/or in vitro. In particular, embodiments of the present disclosure can be used to image non-Hodgkin's lymphoma or related biological events. In this regard, the sample or subject can be tested to determine if the sample or subject includes a non-Hodgkin's lymphoma or related biological conditions, to monitor the progression (or regression) of the non-Hodgkin's lymphoma, or to assess the response of the non-Hodgkin's lymphoma to treatment, to image, and the like. In an embodiment, the tissue or cells can be within a subject or can have been removed from a subject.

In an embodiment, the labeled probe ($^{64}$Cu-FN3 probe) can be imaged using imaging systems such as a positron emission tomography (PET) imaging systems. In an embodiment, PET imaging is a preferred embodiment. Other types of labeled probes can use appropriate imaging systems.

In an embodiment, the labeled probe can be used in diagnosing, localizing, monitoring, and/or assessing non-Hodgkin's lymphoma, cancers, tumors, precancerous cells, and related biological events. In particular, the present disclosure includes methods relating to non-invasive imaging (e.g., using positron emission tomography (PET) imaging system) using the labeled probe in vivo.

The CD20 antigen is present in greater than 90% of B-cell lymphomas and is neither degraded nor internalized after antibody binding. Although antibodies are effective for targeting the CD20 antigen, antibodies are not ideal for radiological use since they have modestly high liver uptake and their slow clearance yields low tumor-to-blood ratios, which necessitates acquiring imaging time points days after administration.

Embodiments of the present disclosure include labeled probes that can be used to target an extracellular peptide loop (amino acids 165-185) of the CD20 antigen: GGYNCEPANPSEKNSPSTQYCYS (SEQ ID NO: 1). In an embodiment, the labeled probe can include a sequence that has an affinity for the extracellular peptide loop (amino acid 165 to 185) of the human CD20 domain. In an embodiment, the labeled probe is a modified fibronectin type 3 (FN3) domain that has been engineered to have affinity for the extracellular peptide loop of human CD20 domain. In an embodiment, the labeled probe can include the following sequence: ASVSDVPRDLEVVAATPTSLLISWCRQRCADSYRITYGETGGNSPVQEFTVPGSWKT ATISGLKPGVDYTITVYVVTHYYGWDRYSHPISINYRTGSHHHHHH (FN3 scaffold, FN3$_{CD20}$, also called "FN3" herein) (SEQ ID NO: 2), variants thereof, homologs thereof, mutants thereof, isolated polypeptides of this sequence, and the like. In embodiments, the labeled probes of the present disclosure are variants of a wild type human FN3 domain (FN3$_{WT}$) (SEQ ID NO: 3) that have been modified to have affinity for (e.g., bind to the extracellular loop of the CD20 antigen). Some variants of FN3$_{CD20}$ include FN3$_{CD20-01}$, (SEQ ID NO: 4), FN3$_{CD20-02}$, (SEQ ID NO: 5) and FN3$_{CD20-03}$, (SEQ ID NO: 6).

Homologs or polypeptides (or fragments thereof) that vary in sequence from the amino acid sequence of the subject disclosure (FN3) (SEQ ID NO: 2) are also provided as long as they retain the characteristics (e.g., biological properties) of the primary sequence (e.g., binding to the CD20 antigen). By homolog is meant a polypeptide having at least about 60%, at least about 65%, at least about 70%, at least about 75%, at least about 80%, at least about 85%, at least about 90%, at least about 95%, and at least about 99% or higher, amino acid sequence identity to the peptide of the subject disclosure, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153, which is hereby incorporated by reference. (Parameters used are ktuple 1, gap penalty 3, window, 5 and diagonals saved 5).

Also provided are polypeptides that are substantially identical to the specifically described subject polypeptides herein (FN3), whereby "substantially identical" is meant that the polypeptide has an amino acid sequence identity to the subject polypeptide of at least about 60%, at least about 65%, at least about 70%, at least about 75%, at least about 80%, at least about 85%, at least about 90%, and at least about 95%, where in some instances the identity may be higher as long as they retain the characteristics (e.g., biological properties) of the primary sequence (e.g., binding to the CD20 antigen).

In representative embodiments, the subject homologues have structural features found in the above provided specific sequence (FN3), where such structural features include binding to the CD20 antigen as described herein.

Proteins that are mutants of the specifically described subject polypeptides (FN3) herein are also provided. Mutants may retain biological properties of the parent as long as they retain the biological properties of the primary sequence The term "biological property" of the subject proteins includes, but is not limited to, binding to the CD20 antigen. Mutants include single amino acid changes, deletions of one or more amino acids, N-terminal truncations, C-terminal truncations, insertions, and the like.

Mutants can be generated using standard techniques of molecular biology (e.g., random mutagenesis and targeted mutagenesis). Several mutants are described herein. Given the guidance provided in the Examples, and using standard techniques, those skilled in the art can readily generate a wide variety of additional mutants and test whether a biological property has been altered.

In an embodiment, the labeled probe includes on or more radiolabels. In an exemplary embodiment, the radiolabel can include one or more of the following: $^{64}Cu$, $^{124}I$, $^{76/77}Br$, $^{86}Y$, $^{89}Zr$, $^{68}Ga$, $^{18}F$, $^{11}C$, $^{125}I$, $^{124}I$, $^{131}I$, $^{123}I$, $^{32}Cl$, $^{33}Cl$, $^{34}Cl$, $^{68}Ga$, $^{74}Br$, $^{75}Br$, $^{76}Br$, $^{77}Br$, $^{78}Br$, $^{89}Zr$, $^{186}Re$, $^{188}Re$, $^{90}Y$, $^{86}Y$, $^{177}Lu$, or $^{153}Sm$. In an embodiment, the radiolabel can be $^{64}Cu$, $^{124}I$, $^{76/77}Br$, $^{86}Y$, $^{89}Zr$, or $^{68}Ga$.

In an embodiment, the radiolabel can be chelated with the sequence (e.g., FN3) at one or more positions along the sequence. In an embodiment, the radiolabel can be chelated at one or more of the lysine amino acids in the sequence [e.g., 4 Lysine (10, 20, 21, and 63)] and/or at an N-terminus free amine site in the sequence. In an embodiment, 1, 2, 3, 4, or 5 radiolabels can be present in the labeled probe. In an embodiment, the radiolabels can be chelated to the sequence using a chelator such as DOTA, NOTA, TETA, EDTA, Df, and DTPA, and derivatives of each of these. In an embodiment, the chelator can be DOTA.

In an embodiment, the $^{64}Cu$-FN3 probe includes a label, $^{64}Cu$, that can be used to detect, image, or otherwise identify the $^{64}Cu$-FN3 probe, quantify the amount of $^{64}Cu$-FN3 probe, determine the location of the $^{64}Cu$-FN3 probe (e.g., in imaging), and combinations thereof. In an embodiment, the chelator $^{64}Cu$-FN3 probe for is DOTA. Additional details regarding the $^{64}Cu$-FN3 probe are described in Example 1.

Methods of Use

Embodiments of this disclosure include, but are not limited to: methods of imaging a sample or a subject using the labeled probe (e.g., $^{64}Cu$-FN3 probe); methods of imaging non-Hodgkin's lymphoma (e.g., cancer or tumor) or related biological conditions using the labeled probe (e.g., $^{64}Cu$-FN3 probe); methods of diagnosing non-Hodgkin's lymphoma or related biological conditions using the labeled probe (e.g., $^{64}Cu$-FN3 probe); methods of monitoring the progress of non-Hodgkin's lymphoma or related biological conditions using the labeled probe (e.g., $^{64}Cu$-FN3 probe), and the like.

Embodiments of the present disclosure can be used to image, detect, study, monitor, evaluate, assess, and/or screen, non-Hodgkin's lymphoma or related biological conditions in vivo or in vitro using the labeled probe (e.g., $^{64}Cu$-FN3 probe).

In a particular embodiment, the $^{64}Cu$-FN3 probe can be used in imaging non-Hodgkin's lymphoma. For example, the $^{64}Cu$-FN3 probe is provided or administered to a subject in an amount effective to result in uptake of the $^{64}Cu$-FN3 probe into the non-Hodgkin's lymphoma or tissue of interest. The subject is then introduced to an appropriate imaging system (e.g., PET system) for a certain amount of time (e.g., this depends on radioisotope being used). The non-Hodgkin's lymphoma that takes up the $^{64}Cu$-FN3 probe could be detected using the imaging system. The location of the detected signal from the $^{64}Cu$-FN3 probe can be correlated with the location of the non-Hodgkin's lymphoma. In an embodiment, the dimensions of the location can be determined as well. Other labeled probes of the present disclosure can be used in a similar manner.

In an embodiment, the steps of this method can be repeated at determined intervals so that the location and/or size of the disease can be monitored as a function of time and/or treatment. In particular, the $^{64}Cu$-FN3 probe can find use in a host undergoing chemotherapy or other treatment (e.g., using a drug, radiation, etc.), to aid in visualizing the response of non-Hodgkin's lymphoma to the treatment. In this embodiment, the $^{64}Cu$-FN3 probe is typically visualized and sized prior to treatment, and periodically (e.g., daily, weekly, monthly, intervals in between these, and the like) during chemotherapy, radiotherapy, and the like, to monitor the tumor size. Other labeled probes can be used in a similar manner.

Embodiments of the $^{64}Cu$-FN3 probe also find use as a screening tool in vitro to select compounds for use in treating non-Hodgkin's lymphoma tissue or cells. The non-Hodgkin's lymphoma could be easily monitored by incubating the diseased cells with the $^{64}Cu$-FN3 probe during or after incubation with one or more candidate drugs. The ability of the drug compound to affect the disease can be imaged over time using the $^{64}Cu$-FN3probe. Other labeled probes of the present disclosure can be used in a similar manner.

It should be noted that the amount effective to result in uptake of the labeled probe (e.g., $^{64}Cu$-FN3 probe) into the cells or tissue of interest may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and a labeled probe (e.g., $^{64}Cu$-FN3 probe) of the disclosure. In certain embodiments, the packaged compositions or pharmaceutical composition includes the reaction precursors to be used to generate the labeled probe according to the present disclosure. Other packaged compositions or pharmaceutical compositions provided by the present disclosure further include materials including at least one of: instructions for using the labeled probe to image a host, or host samples (e.g., cells or tissues), which can be used as an indicator of conditions including, but not limited to, non-Hodgkin's lymphoma and biological related conditions.

Embodiments of this disclosure encompass kits that include, but are not limited to, the labeled probe (e.g., $^{64}$Cu-FN3 probe) and directions (written instructions for their use). The components listed above can be tailored to the particular biological condition to be monitored as described herein. The kit can further include appropriate buffers and reagents known in the art for administering various combinations of the components listed above to the host cell or host organism. The imaging agent and carrier may be provided in solution or in lyophilized form. When the imaging agent and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least the labeled probe of the present disclosure, e.g., $^{64}$Cu-FN3 probe) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the labeled probe (e.g., $^{64}$Cu-FN3 probe), pharmaceutically acceptable salts thereof, with other chemical components, such as physiologically acceptable carriers and excipients. One purpose of a pharmaceutical composition is to facilitate administration of labeled probe (e.g., $^{64}$Cu-FN3 probe) to a subject (e.g., human).

Embodiments of the present disclosure may be salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an active compound may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and a specific type of active ingredient (e.g., a labeled probe such as $^{64}$Cu-FN3 probe) in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Introduction

Anti-CD20 monoclonal antibodies, including rituximab, have shown significant utility in patients with non-Hodgkin's lymphoma and have become the basis for treatment. Reliable diagnostic information on CD20 detection is important for effective patient management. Compared to antibodies, the use of small radiolabeled targeting protein ligands would enable high-contrast imaging of cancers at earlier time points due to fast clearance from background tissues. The present example describes engineering the 10 kDa human fibronectin type 3 domain (FN3) for binding to the extracellular peptide loop (amino acids 165-185) of the human CD20 domain. After 6 iterations of selection and affinity maturation, the resultant FN3 binds CD20 with 20 nM affinity on CD20-expressing cells. The engineered FN3 was radiolabeled with $^{64}$Cu and used for positron emission tomography imaging of huCD20 expression in B cells using a humanized transgenic mouse model. The $^{64}$Cu-FN3 showed clear, high-contrast visualization of huCD20-expressing B-cells in the spleen of transgenic mice as early as 1 hour post-injection (38±3% ID/g) and exhibited a spleen-to-blood ratio of 13 by 4 h. This is higher uptake (P=0.04) and ten-fold greater signal-to-background (P=0.04) than the $^{64}$Cu-rituximab antibody radiotracer. $^{64}$Cu-Do-FN3$_{CD20}$ radiotracer represents a novel small, high affinity binder for imaging cancer-specific CD20, which may be well suited for non-Hodgkin's lymphoma imaging in patients at early time points.

The CD20 antigen is present in greater than 90% of B-cell lymphomas and is neither degraded nor internalized after antibody binding, making it an effective target for immunotherapeutic removal of malignant B cells (1-3). In the plasma membrane, CD20 is predicted to contain two extracellular loops, a larger one between the third and fourth transmembrane regions, and a much smaller one between the first and second transmembrane regions (4, 5) Immunotherapies using monoclonal antibodies targeting B cell surface antigens have been widely accepted for the treatment of non-Hodgkin lymphomas (NHL), with anti-CD20 antibodies being most commonly employed (1). Rituximab, a chimeric anti-CD20 antibody, has provided the best clinical results to date with single-agent remission induction rates of >60% in patients with indolent lymphomas and 30% to 35% in relapsed aggressive lymphomas (2-4). However, for imaging, radiolabeled antibodies provide high tumor signal (8% injected dose [ID]/g) but also modestly high liver uptake (2-11% ID/g), and slow clearance yields low tumor-to-blood ratios (≤0.5) (6, 7) and therefore necessitate late imaging time points (days).

Compared to antibodies, lower molecular weight protein scaffolds can provide faster clearance and demonstrate specific in vivo targeting ability to yield excellent tumor-to-background contrast (8). Validated scaffolds include, e.g., antibodies (8-10), knottins (11, 12), nanobodies (13, 14), peptides (15), antibody fragments (16-19), and the 10th type III domain of human fibronectin (FN3) (20). FN3 is a 10 kDa β-sandwich that has been engineered for picomolar to nanomolar affinity binding to many targets (20, 21) and has been validated for molecular imaging in murine xenograft tumor models (22). The size of FN3 (8% of antibody size) balances rapid clearance from blood and background tissues while having enough surface area for in vivo targeting specificity. Its small size aids vascular extravasation (23) and tissue penetration to improve solid tumor delivery (24, 25). FN3 structure contains three solvent-exposed loops that can be mutated to introduce new high affinity binding activity (20, 26, 27). High stability and a single lysine distant from the paratope ease amine conjugation of radioisotopes. In addition to preclinical molecular positron emission tomography (PET) validation, an engineered FN3 is in phase II for therapeutic oncology (28).

The present example describes selection, production and characterization of an FN3 protein scaffold targeting human CD20 antigen. Further we have utilized this molecule for pre-clinical PET imaging to assess the ability to achieve more rapid, higher contrast imaging compared to the full antibody.

Materials and Methods
Reagents and Radiochemicals

All reagents were obtained from Sigma-Aldrich (St. Louis, Mo.) unless otherwise stated. N-succinimidyl-DOTA (NHS-DOTA) was purchased from Macrocyclics (Dallas, Tex., USA). The CD20 positive B-cell lymphoma cell line Ramos and CD20-negative Jurkat cells were obtained from the American Type Culture Collection (ATCC numbers: CRL-1555 and TIB-152). Ramos cells were maintained in Dulbecco's modified Eagle's medium (4.5 g/L glucose), Jurkat cells in MEM/Ham's F-12 (1:1), and 1% nonessential amino acids. All media were supplemented with 10% fetal calf serum, 2 mmol/L glutamine, 100 units/mL penicillin, 100 µg streptomycin, and 0.25 µg/mL fungizone. All media and additives were obtained from Life Technologies (Carlsbad, Calif. USA).

High-performance liquid chromatography (HPLC) was performed on HPLC-Ultimate 3000 with an ultraviolet detector and an online radioactivity detector. The system used a SEC 2000 LC column (300×7.8 mm) with 5 µm hydrophilic bonded silica support and 400 Å pore size (Phenomenex, Torrance, Calif. 90501-1430, USA). Matrix-assisted laser desorption ionization mass spectrometry was performed with an AB SCIEX TOF/TOF 5800 operated in linear mode with sinapinic acid as matrix.

Engineering of $FN3_{CD20}$

The human CD20 peptide extracellular loop was synthesized (amino acids: 165-185; GG YNCEPANPSEKNSPSTQYCYS (SEQ ID NO: 1)-biotin) and purified by RP-HPLC on a C-18 column and lyophilized as per the published procedure (29). This peptide was characterized by ESI-MS and immobilized on streptavidin magnetic beads for screening of FN3 binders. The yeast surface displayed FN3 G4 library with diversified loops and was sorted and matured as described (26, 30). Briefly, yeast displaying $2.5 \times 10^8$ FN3 mutants were sorted for binding to magnetic beads with immobilized CD20 peptide, followed by fluorescence-activated cell sorting for full-length proteins using the C-terminal c-myc epitope. Plasmid DNA from selected clones was recovered, mutated by error-prone PCR of either the entire FN3 gene or the paratope loops, and reintroduced into yeast by electroporation with homologous recombination. As binder enrichment progressed in later evolutionary cycles, fluorescence-activated cell sorting for binding to soluble CD20 peptide was also used. Six cycles of selection and mutation were performed. Plasmid DNA was recovered, transformed into bacteria, and individual clones were sequenced by standard DNA sequencing methods.

Preparation of $FN3_{CD20}$

Bacterial expression plasmids were constructed to express either the 101—amino acid $FN3_{CD20}$ or a nonbinding control ($FN3_{WT}$) (SEQ ID NO: 3), which is the human wild type sequence except the arginine-glycine—aspartic acid sequence was mutated to arginine-aspartic acid-glycine (FIG. 1A). The plasmids also encode for a C-terminal $His_6$ epitope tag for purification. Plasmids were transformed into BL21 (DE3) *Escherichia coli*. Cells were grown in 1 L of lysogeny broth medium and induced with 0.5 mmol/L isopropyl β-D-1-thiogalactopyranoside for 1 hour. Cells were pelleted, resuspended in 10 mL of lysis buffer (50 mmol/L sodium phosphate, pH 8.0, 500 mmol/L sodium chloride, 5% glycerol, 5 mmol/L CHAPS detergent, 25 mmol/L imidazole, and complete ethylenediaminetetraacetic acid-free protease inhibitor cocktail), frozen and thawed, and sonicated. The sample was centrifuged at 12,000×g for 10 minutes. Fibronectin was purified from the soluble fraction by immobilized metal affinity chromatography and reversed-phase high-performance liquid chromatography was performed with a C18 column. Protein mass was verified by mass spectrometry. Determination of binding constants by surface plasmon resonance (SPR)

All measurements were performed at 25° C. on a BIAcore 100 instrument and streptavidin chip (GE healthcare Biosciences, PA). The streptavidin chip was first cleaned with three consecutive 1-min. injections of 40 µl, of a solution of 1 M NaCl in 50 mM NaOH before the immobilization procedure. Five minutes after the cleaning process when the sensorgram reached a stable baseline, biotynalated CD20 peptide, diluted in running buffer to 20 µg/mL, was injected for 7 min. using a flow rate of 5 µL/min. The same procedure was performed for immobilization of non-specific CD20 peptide, except that the non-specific CD20 peptide was diluted in running buffer to 200 µg/ml. To attain maximum immobilization level of biotin peptides on the surface of streptavidin, multiple injections were performed.

Target antigen of CD20 peptide was immobilized on a streptavidin chip. $FN3_{CD20}$ was analyzed in 10 mM HEPES, pH 7.4, 150 mM NaCl, 0.005% Tween 20 at five concentrations between 0 and 750 nM, and non-specific FN3 was used as control. The flow-rate was 15 µl/min; association and dissociation times were 1 and 2 min, respectively. Each concentration sample was assayed in duplicate and the response from an empty flow cell and from buffer injections was subtracted from each data set. The data were analyzed using BIAeval (BIAcore) software, with a global fitting to the 1:1 binding model. There were no indications of mass transport-limited kinetics or of other complications.

Intact Cell Binding Flow Cytometry Assay

Cells were incubated at 37° C. in humidified air with 5% $CO_2$. For affinity measurement, $1 \times 10^5$ Ramos or Jurkat cells were washed with PBS with 0.1% bovine serum albumin and incubated with various concentrations of fibronectin. Cells were pelleted, washed with PBS with 0.1% bovine serum albumin, and incubated with fluorophore-conjugated anti-$His_6$ antibody in PBS with 0.1% bovine serum albumin. Cells were washed and analyzed by using flow cytometry. The minimum and maximum fluorescence and the affinity value were determined by minimizing the sum of squared errors assuming a 1:1 binding interaction. Experiments were performed in triplicate.

Preparation of Do-$FN_3$

The DOTA-NHS ligand has already shown good biological performance when used in protein conjugation of various radionuclides such as $^{66}$Ga, $^{68}$Ga, $^{177}$Lu, $^{225}$Ac and lead radionuclides (31). DOTA-FN3 (Do-FN3) tracer was prepared by conjugating DOTA-NHS to FN3 according to a published procedure (22). Briefly, lyophilized FN3 protein was resuspended in dimethylformamide with 2% triethylamine, and reacted at room temperature for 1 hour with 20 equivalents of DOTA-NHS. DOTA-FN3 was purified by HPLC and lyophilized for $^{64}$Cu labeling. The number of DOTA chelators conjugated to each FN3 molecule was calculated by mass spectrometry by comparing the mass of FN3 and Do-FN3 (32, 33).

Radiolabeling of Do-FN3

The radiolabeling of Do-FN3 with $^{64}$CuCl$_2$ (University of Wisconsin, Madison, Wis., USA) was carried out as follows. Do-FN3, 25 to 50 µg in 100 µl of 0.25 mol/L ammonium acetate buffer (pH 5.5) was reacted with 92.5 to 185 MBq of neutralized $^{64}$CuCl$_2$ solution at 37° C. of pH 5.5 for 1 h. After incubation, 0.1 M diethylenetriaminepentaacetic acid, pH 7.0, was added to a final concentration of 5 mM and incubated at room temperature for 15 min. to scavenge unchelated $^{64}$CuCl$_2$ in the reaction mixture. Purification of the $^{64}$Cu-Do-FN3 was achieved using reversed-phase high-performance liquid chromatography (Torrance, Calif., USA) with a flow rate of 1.0 ml/min followed by rotary evaporation of solvent and dilution in PBS [0.1 mol/L NaCl, 0.05 mol/L sodium phosphate (pH 7.4)]. The final radioconjugate of $^{64}$Cu-Do-FN3 was filtered through a 0.2 µm filter into a sterile vial.

Radiotracer Cell binding Assay

For a cell culture radiolabeled binding assay, 1×10$^5$ cells were aliquoted in each tube, washed with PBS, and incubated with 25 nM $^{64}$Cu-FN3$_{CD20}$ (10-20 MBq/nmol) for 30 minutes. Cells were washed thrice with PBS. Activity in each tube of cell pellet was quantified with a gamma ray counter (1470 WIZARD Automatic Gamma Counter; Perkin-Elmer, Waltham, Mass.).

Small Animal PET Imaging

Animal studies were performed in compliance with approval from the Administrative Panel on Laboratory Animal Care at Stanford University. The huCD20 transgenic mice (Genentech, South San Francisco) were purchased for the experiments (32, 34). Prior to the imaging study, huCD20 transgenic mice were screened to confirm the expression of CD20 positive targets by RT-PCR. The average weight of the mice was 25.0±2.0 g. Mice (3 per group) were lightly restrained and administered the dose of $^{64}$Cu-Do-FN3 (3.7 MBq/4 µg Do-FN3 in 200 µL PBS) via a lateral tail vein. One group also received a blocking dose (50-fold excess) of unconjugated FN$_{CD20}$ two hours prior to radiotracer injection. At each time point (1, 2, 4, 16, and 24 h post-injection) the animals were anesthetized and imaged on a Siemens Inveon small-animal multimodality PET/CT system (Preclinical Solutions; Siemens Healthcare Molecular Imaging, Knoxyille, Tenn.). This PET/CT system combines two independently operating PET and CT scanners with radial, tangential, and axial resolutions of 1.5 mm at the center of the field of view of the PET module. The CT raw images were acquired at 80 kVp at 500 µA, two bed position, half-scan 220° of rotation, and 120 projections per bed position with a cone beam micro-X-ray source (50-µm focal spot size) and a 2048×3072 pixel X-ray detector. CT raw data sets were reconstructed using Shepp-Logan filter and cone-beam filtered back-projection. On the basis of attenuation correction from the CT measurements, static PET scan was acquired with default settings of coincidence timing window of 3.4 ns and energy window of 350 to 650 keV. The first acquisition was started 1 h after the tracer injection and acquired for 5 min. We then performed 5 min acquisitions after 2, 4 and 16 h and 10 min scan after 24 h tracer injection. The images were reconstructed with two-dimensional ordered-subset expectation maximization (OSEM 2D) algorithm. (35) Image files were analyzed using a Medical Image Data Examiner (AMIDE) open source software or Inveon Research Workspace (IRW). (36) For each small animal PET scan, three-dimensional regions of interest (ROIs) were drawn over the heart, liver, spleen, kidneys, and muscle on decay-corrected whole-body images. The average radioactivity concentration in the ROI was obtained from the mean pixel values within the ROI volume. These data were converted to counts per milliliter per minute by using a predetermined conversion factor. The results were then divided by the injected dose to obtain an image region of interest-derived % ID/g. Statistical analysis was done with Student's t test (two-tailed, unequal variance).

Results

Engineering and Characterization of FN3$_{CD20}$

After six iterations of selection and maturation, four dominant clones (SEQ ID NOs: 2, 4, 5 and 6) were identified by sequence analysis (FIG. 1A). Affinity titrations with yeast surface display and flow cytometry indicated that one clone showed the best dissociation constant ($K_d$) 14.3±1.3 nM for binding to biotynalated CD20. This clone also exhibits target specificity, as it does not show appreciable binding towards a scrambled CD20 peptide. This clone, named FN3$_{CD20}$ (SEQ ID NO: 2), was produced in bacterial culture with a His6-tag and purified by nickel column chromatography and reversed-phase high performance liquid chromatography with >95% purity. Mass spectrometry showed 11,560 Da molecular weight (expected 11,561 Da). Surface plasmon resonance demonstrates the affinity of FN3$_{CD20}$ for CD20 peptide (amino acids 165-185) was 22 nM. (FIG. 1B). A flow cytometry assay with live Ramos cells, which express CD20 antigens, indicates a binding affinity for cellular CD20 as 20±2.0 nM (FIG. 1C).

Production and Characterization of $^{64}$Cu-Do-FN3

The anti-CD20 FN3 binder was conjugated with DOTA-NHS (FIG. 2A) for in vitro live cell binding assay and in vivo animal imaging study. DOTA was conjugated to primary amines on FN3$_{CD20}$ with a yield of 1.8 DOTA molecules per FN3 protein as measured by mass spectrometry. Radiolabeling of Do-FN3 with $^{64}$Cu in ammonium acetate buffer (pH 5.5) was performed with 80.0±3.1% yield. The highest radiochemical yield achieved was 85% at 37° C., of pH 5.5, at incubation for 60 min. Radiochemical purity was 97.0±0.5% as determined by HPLC.

Figure 3:
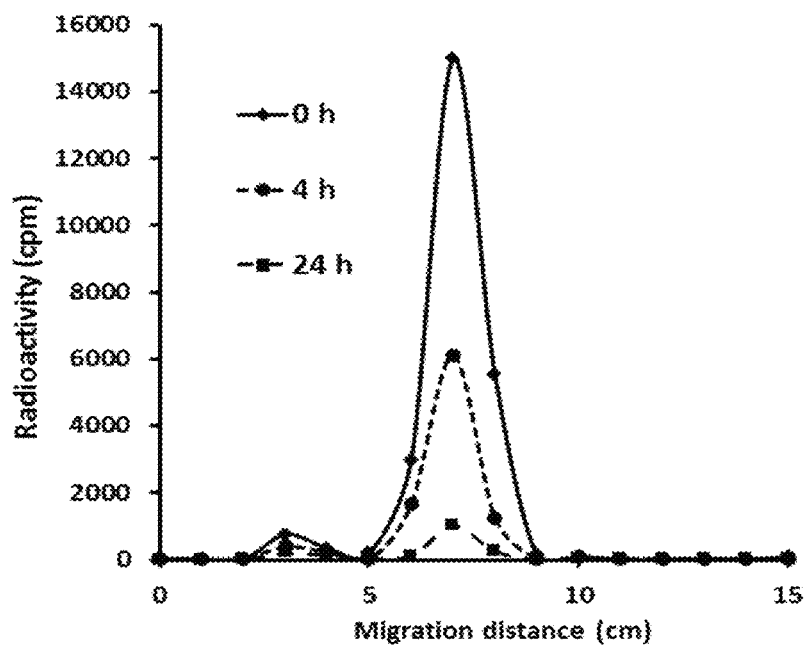
FIG. 3 illustrates a graph of the serum stability of $^{64}$Cu-Do-FN3$_{CD20}$ assayed by cellulose acetate electrophoresis (CAE). Radioconjugate (25 mg) was mixed with 1 mL of human serum and incubated at 37° C. At various time points (0, 4, and 24 h), 10 µL samples were drawn and tested for stability on CAE. CAE was performed for 45 min with barbital buffer (0.05 M, pH 8.6) at room temperature. Note that radioactivity is not decay-corrected to enable clearer visualization of the consistent migration distance.

The immunoreactivity and specificity of $^{64}$Cu-Do-FN3 radio tracer was tested in live Ramos (CD20$^+$) and Jurkat (CD20$^-$) cells. Twenty five nanomolar $^{64}$Cu-Do-FN3 readily bound to Ramos cells, whereas the non-binding control $^{64}$Cu-Do-FN3$_{WT}$ exhibited only background signal (P<0.001); moreover, binding was inhibited by the addition of 1000 nM unlabeled FN3$_{CD20}$ (P<0.005) (FIG. 2B). CD20 specificity was further demonstrated by the reduced binding to Jurkat cells, which lack appreciable CD20 expression. Thus, $^{64}$Cu-Do-FN3 was a specific tracer for CD20 antigen. $^{64}$Cu-Do-FN3$_{CD20}$ PET tracer is stable in human serum as it remains >95% intact for up to 24 h (FIG. 3).

Small Animal PET Imaging

To evaluate the in vivo targeting ability of the $^{64}$Cu-Do-FN3$_{CD20}$ PET tracer, a humanized transgenic mouse model that expresses human CD20 antigens on B-cells (huCD20TM) was used to mimic a human B-cell lymphoma tumor. From the PET/CT data (FIGS. 4, 5, and Supplemental Movie), it is evident that $^{64}$Cu-Do-FN3$_{CD20}$ had significant uptake in the spleen, the major site for B cells, which express the CD20 antigen. Spleen uptake was 38±3% ID/g within 1 h post-injection and increased to 85±4% ID/g at 24 h. Notably, pre-administration of 50-fold excess of unlabeled FN3$_{CD20}$ dramatically reduces spleen uptake (P=0.005, 0.0004, 0.01, at 4, 16, and 24 h, respectively, FIG. 5A). Specificity is further demonstrated as the non-targeted control $^{64}$Cu-Do-FN3$_{WT}$ exhibits low spleen uptake: 4.8±0.6, 8.3±0.3, 10.4±0.9% ID/g (P=0.02, 0.01, 0.01) at 4, 16, and 24 h respectively.

At 24 h the tracer uptake value of liver and kidney of non-blocking mice were 50±2, and 14±3 respectively, while blocking mice exhibited 10.6±0.5 and 5.3±0.9 for liver and kidney, respectively measured by ROI (FIG. 5B). After 24 h post injection two groups of mice (blocking and non-blocking) organs were resected and counted for the tracer uptake (FIG. 6). Overall study results of both in vivo and ex vivo correlate well. Moreover, ex vivo studies show low tracer uptake by background tissues: 1.2±0.6% ID/g in blood and 0.28±0.11% ID/g in muscle. The ratio of tracer target-to-background tissue (spleen/blood) is 56±5, which is significantly decreased in pre-blocked mice (8.8±1.7, P=0.03) by ex vivo measurement.

To assess the impact of the protein scaffold and evaluate translational potential for PET imaging, $^{64}$Cu-Do-FN3$_{CD20}$ was compared to our previous data (32) for $^{64}$Cu-rituximab within the identical huCD20TM model. The $^{64}$Cu-Do-FN3$_{CD20}$ tracer uptake value in spleen was significantly higher, compared to the $^{64}$Cu-rituximab mice group. The uptake values of $^{64}$Cu-FN3 and $^{64}$Cu-rituximab are 38.0±1.8 and 31.8±1.6 (P=0.041) for 1 h, and 46±2 and 35±2 (P=0.037) for 4 h, respectively (FIG. 7A). The spleen-to-blood ratios for the FN3 and $^{64}$Cu-rituximab tracers are 13±1 and 1.34±0.03 at 4 h (FIG. 7B), which are also highly statistically significant (P<0.005).

Discussion

CD20 has proven to be a promising target for therapy of NHL (37). Development of an imaging agent would have significant value for monitoring disease progression and therapeutic efficacy. Several antibodies targeting CD20 have been tested for their potential for therapy and molecular imaging (38). The present example describes the development of a novel radiotracer based on the FN3 protein scaffold, which is 8% of the antibody size and thereby provides more rapid clearance and potentially more effective distribution. On the contrary, intact antibodies generally have slow distribution and clearance. The accumulation in tumor tissue and clearance from the circulation can take several (3-10) days (39, 40). The intent was to develop a tracer to achieve quantitative visualization of tumors by PET at an early time point, preferably within 12 hours after tracer injection; this would be beneficial clinically and could substantially reduce normal tissue radiotoxic burden.

Figure 4:
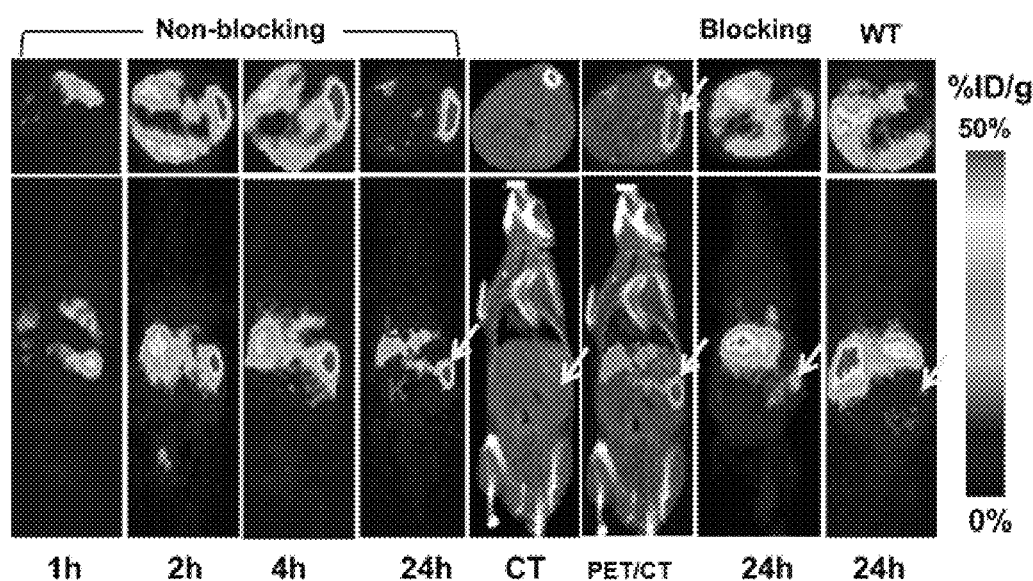
FIG. 4 illustrates small animal PET images showing the $^{64}$Cu-Do-FN3$_{CD20}$ tracer in huCD20 transgenic mice. The PET, CT and PET/CT images on top and bottom rows are transverse and coronal views, respectively. PET images were obtained at 1, 2, 4 and 24 time points after tail-vein injection of $^{64}$Cu-Do-FN3$_{CD20}$ tracer (3.7 MBq). The CT and PET/CT co-registered images are shown at 24 h after tracer injection for organ identification. Non-blocking mice were injected with tracer alone. Blocking mice were pre-blocked with 50-fold excess of unconjugated FN3$_{CD20}$ over tracer mass 2 h prior to tracer injection. The spleen (tracer targeting cells in this organ) is indicated by the arrow. The other major clearance organs are marked in the letters "L" and "K" (Liver and Kidney). WT: Wild type. The color scale bar shows tracer % ID/g.
Figure 7:
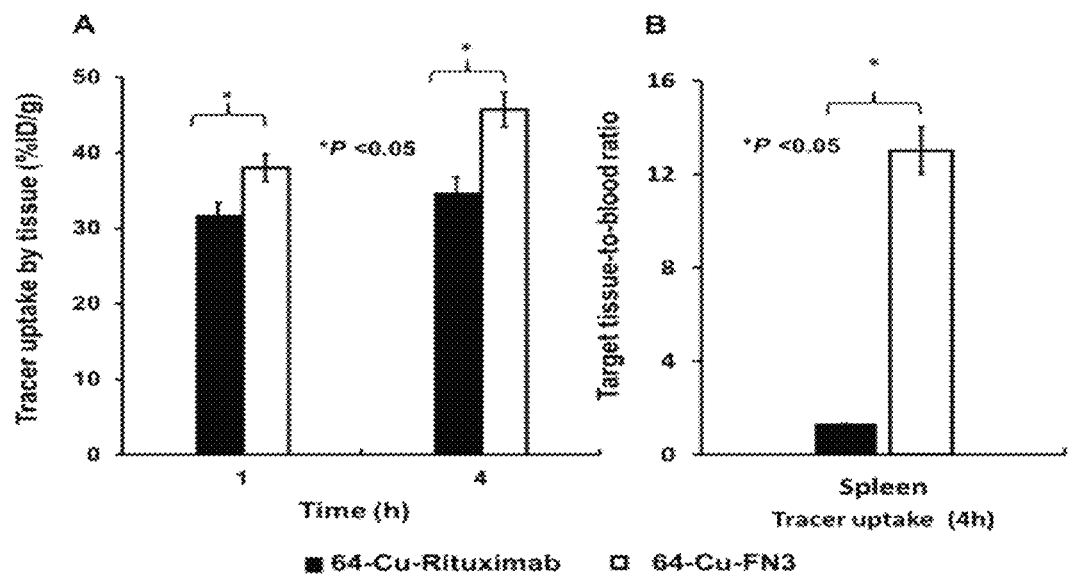
FIG. 7A illustrates a graph of a comparison of two different lymphoma PET tracers tested against huCD20 target in huCD20 transgenic mice (n=3). Tracer uptake values (mean±standard deviation) of two tracer groups of non-blocking mice were measured and compared at 1 and 4 h respectively. The $^{64}$Cu-FN3$_{CD20}$ tracer uptake value in spleen was significantly higher than $^{64}$Cu-rituximab.
FIG. 7B illustrates a graph at 4 h tracer uptake value (mean % ID/g±SD) in the spleen and blood of two tracer groups of non-blocking mice measured by ex vivo and compared for spleen-to-blood ratio of $^{64}$Cu-rituximab and $^{64}$Cu-FN3$_{CD20}$.

The FN3-based protein scaffold system demonstrates potential as a useful scaffold for imaging agents (20, 41). FN3 domains can be readily engineered for specific, high affinity binding, retain good stability, and are derived from a human parental sequence, which may limit immunogenicity (41). The present example demonstrates the development of FN3-based binders for CD20, screened and selected against immobilized CD20 peptide and intact lymphoma cells by established methods (22). The resulting, soluble FN3 protein provides high affinity CD20 binding as tested by surface plasmon resonance (FIG. 1B, $K_D$=22 nM) and a live cell binding assay (FIG. 1C, $K_D$=20 nM). Monovalent FN3$_{CD20}$ exhibits comparable binding affinity to rituximab antibody ($K_D$=8 nM, (42)), and faster clearance of FN3 binder from blood and background tissues enables visualization of the target tissue more clearly and sooner than antibody based PET (FIGS. 4 and 7). The stability of the FN3 scaffold and the DOTA chelator yield a radiotracer that remains >95% intact for 24 h in human serum (FIG. 3).

Figure 5:
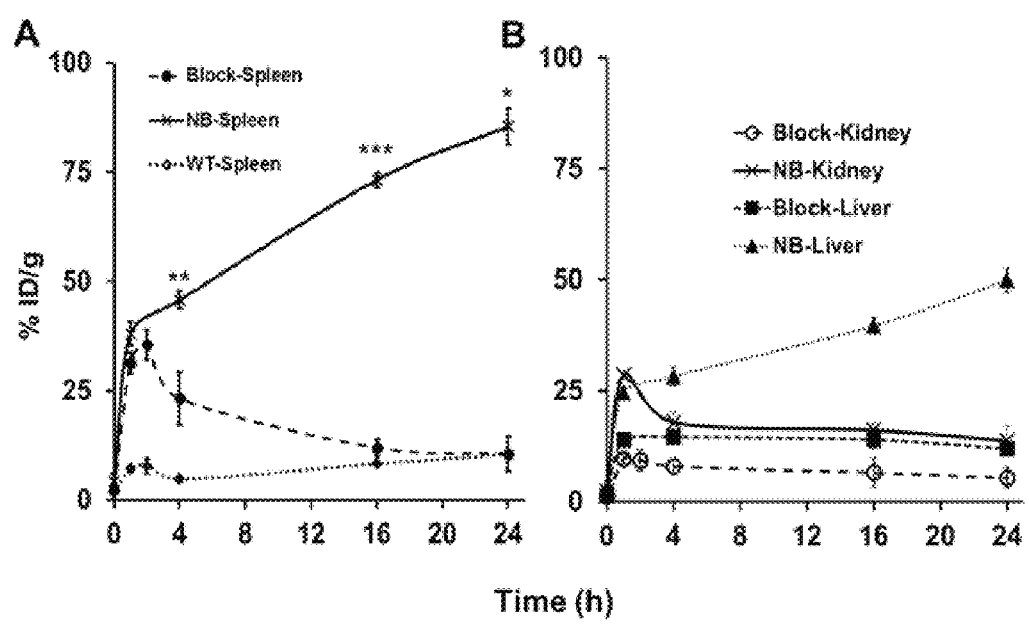
FIGS. 5A and 5B illustrates the $^{64}$Cu-Do-FN3$_{CD20}$ tracer signals in targeting and clearance organs of huCD20 transgenic mice by quantification of images in FIG. 4. Regions of interest were drawn around the spleen (FIG. 5A), liver (FIG. 5B), and kidney (FIG. 5B), and activity was quantified. The percent injected dose per gram (% ID/g) of each organ is presented at 1, 2, 4, 16, and 24 h post-injection (mean±standard deviation; n=3). Pre-block mice received 8 mg/kg pre-dose of unconjugated FN3$_{CD20}$ 2 h prior to tracer injection (i.v., dose 3.7 MBq), and non-block (NB) mice received no pre-dose. *=P<0.01, =P<0.005, *=P<0.0005.
Figure 6:
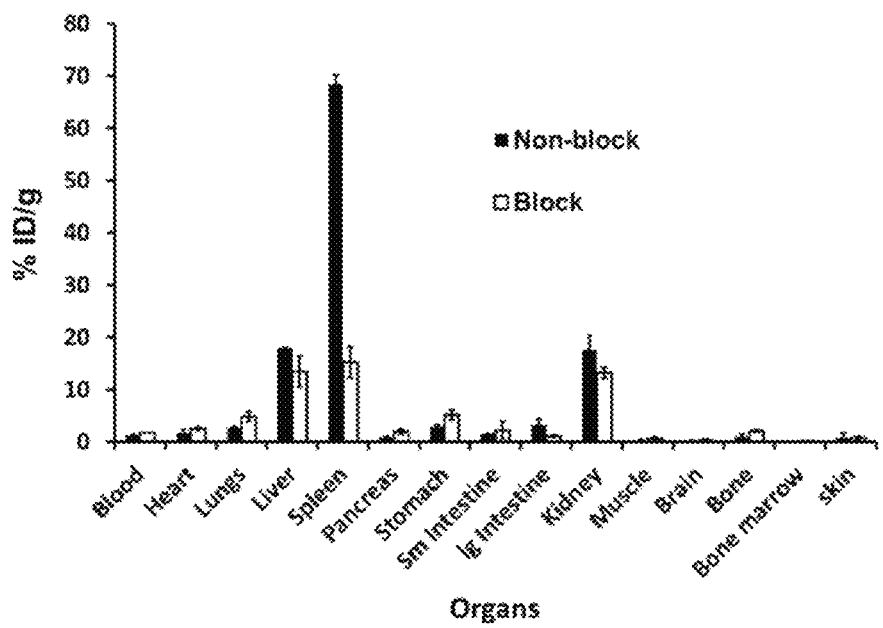
FIG. 6 illustrates a graph of a $^{64}$Cu-Do-FN3$_{CD20}$ tracer biodistribution in huCD20 mice (n=3). The huCD20 mice were injected with 3.7 MBq of $^{64}$Cu-Do-FN3$_{CD20}$ tracer and euthanized at 24 h post-injection. Organs were isolated and percent injected dose per gram of tissue (% ID/g) were decay corrected. Organs uptake of tracer dose was measured (mean % ID/g±SD) after 24 h post injection. Pre-block mice received 8 mg/kg pre-dose of unconjugated FN3$_{CD20}$ 2 h prior to tracer injection (i.v., dose 3.7 MBq), and non-block (NB) mice received no pre-dose.

$^{64}$Cu-FN3$_{CD20}$ tracer rapidly and durably targeted the spleen, which is the dominant location of CD20-positive B cells, as evidenced by 38% ID/g uptake at 1 h and increasing signal to 85% ID/g at 24 h (FIGS. 5 and 6). This targeting is specific as pre-blocking with cold FN3$_{CD20}$ substantially reduces the spleen signal (FIGS. 4 and 5). Moreover, non-targeted control $^{64}$Cu-FN3$_{WT}$ uptake by spleen was only 10% ID/g (FIG. 4) at 24 h. The $^{64}$Cu-DOTA-rituximab tracer was previously developed and tested in the huCD20TM model, and is now undergoing a clinical trial (32) under a US FDA IND (#104995). The current FN3-based tracer performs favorably relative to this previous antibody tracer. Spleen uptake in the huCD20TM model is higher at 1 and 4 h (FIG. 8A) and target tissue-to-blood ratio is 10-fold higher (FIG. 7B). It should be noted that these results were obtained with a transgenic mouse model, which should prove to be more representative of human tumor development than typical subcutaneous xenograft models.

While $^{64}$Cu-Do-PN3$_{CD20}$ rapidly clears from most tissues, liver and kidney signal are more prevalent. Liver activity may be due to dissociation of $^{64}$Cu from DOTA (43) or charge effects of the engineered protein and the DOTA chelator. Kidney retention is a common problem for small proteins (38) since they pass through the glomerulus and can be reabsorbed in the renal tubules. The renal retention of $^{64}$Cu-Do-FN3$_{CD20}$ is actually much lower than many other comparably sized $^{64}$Cu-DOTA-labeled molecules (38). Spleen uptake remains substantially higher than liver (1.7±0.1 fold) and kidney (3.7±2.1) (FIG. 5). The results of the present study and others (38, 44) demonstrate that smaller binders can provide better imaging results compared to high molecular weight antibodies both in terms of tumor-to-blood ratio and absolute tumor uptake. From the patient perspective, the development of a PET tracer to visualize CD20 at early time-points in human patients could provide valuable clinical insight while reducing the radioactivity burden by healthy tissue.

Thus, the present example demonstrates a novel CD20-targeted PET radiotracer based upon a small FN3 protein scaffold. The radiotracer specifically binds to CD20 proteins on B cells both in culture and in vivo. This novel tracer may provide superior CD20 molecular imaging signal to background for NHL at early time points compared to an intact antibody.

References, each of which is incorporated herein by reference for the relevant discussion 1. Maloney D G. Immunotherapy for non-Hodgkin's lymphoma: monoclonal antibodies and vaccines. Journal of clinical oncology: official journal of the American Society of Clinical Oncology. 2005; 23:6421-8.
2. Tedder T F, Engel P. CD20: a regulator of cell-cycle progression of B lymphocytes. Immunology today. 1994; 15:450-4.
3. Tedder T F, Streuli M, Schlossman S F, Saito H. Isolation and structure of a cDNA encoding the B1 (CD20) cell-surface antigen of human B lymphocytes. Proceedings of the National Academy of Sciences of the United States of America. 1988; 85:208-12.
4. Polyak M J, Tailor S H, Deans J P. Identification of a cytoplasmic region of CD20 required for its redistribution to a detergent-insoluble membrane compartment. Journal of immunology. 1998; 161:3242-8.
5. Teeling J L, Mackus W J, Wiegman U, van den Brakel J H, Beers S A, French R R, et al. The biological activity of human CD20 monoclonal antibodies is linked to unique epitopes on CD20. Journal of immunology. 2006; 177: 362-71.
6. Pagel J M, Hedin N, Subbiah K, Meyer D, Mallet R, Axworthy D, et al. Comparison of anti-CD20 and anti-CD45 antibodies for conventional and pretargeted radioimmunotherapy of B-cell lymphomas. Blood. 2003; 101:2340-8.

7. Sharkey R M, Karacay H, Litwin S, Rossi E A, McBride W J, Chang C H, et al. Improved therapeutic results by pretargeted radioimmunotherapy of non-Hodgkin's lymphoma with a new recombinant, trivalent, anti-CD20, bispecific antibody. Cancer Res. 2008; 68:5282-90.
8. Miao Z, Ren G, Liu H, Jiang L, Cheng Z. Small-animal PET imaging of human epidermal growth factor receptor positive tumor with a 64Cu labeled affibody protein. Bioconjugate chemistry. 2010; 21:947-54.
9. Nordberg E, Orlova A, Friedman M, Tolmachev V, Stahl S, Nilsson F Y, et al. In vivo and in vitro uptake of 111In, delivered with the affibody molecule (ZEGFR:955)$_2$, in EGFR expressing tumour cells. Oncology reports. 2008; 19:853-7.
10. Tolmachev V, Rosik D, Wallberg H, Sjoberg A, Sandstrom M, Hansson M, et al. Imaging of EGFR expression in murine xenografts using site-specifically labelled anti-EGFR 111In-DOTA-Z EGFR:2377 Affibody molecule: aspect of the injected tracer amount. European journal of nuclear medicine and molecular imaging. 2010; 37:613-22.
11. Jiang L, Kimura R H, Miao Z, Silverman A P, Ren G, Liu H, et al. Evaluation of a 64Cu-Labeled Cystine-Knot Peptide Based on Agouti-Related Protein for PET of Tumors Expressing αvβ3 Integrin. Journal of Nuclear Medicine. 2010; 51:251-8.
12. Kimura R H, Cheng Z, Gambhir S S, Cochran J R. Engineered Knottin Peptides: A New Class of Agents for Imaging Integrin Expression in Living Subjects. Cancer Research. 2009; 69:2435-42.
13. Gainkam L O T, Huang L, Caveliers V, Keyaerts M, Hernot S, Vaneycken I, et al. Comparison of the Biodistribution and Tumor Targeting of Two 99 mTc-Labeled Anti-EGFR Nanobodies in Mice, Using Pinhole SPECT/Micro-CT. Journal of Nuclear Medicine. 2008; 49:788-95.
14. Huang L, Gainkam L O, Caveliers V, Vanhove C, Keyaerts M, De Baetselier P, et al. SPECT imaging with 99 mTc-labeled EGFR-specific nanobody for in vivo monitoring of EGFR expression. Molecular imaging and biology: MIB: the official publication of the Academy of Molecular Imaging. 2008; 10:167-75.
15. Chen X, Hou Y, Tohme M, Park R, Khankaldyyan V, Gonzales-Gomez I, et al. Pegylated Arg-Gly-Asp Peptide: 64Cu Labeling and PET Imaging of Brain Tumor αvβ3-Integrin Expression. Journal of Nuclear Medicine. 2004; 45:1776-83.
16. Cai W, Chen K, He L, Cao Q, Koong A, Chen X. Quantitative PET of EGFR expression in xenograft-bearing mice using 64Cu-labeled cetuximab, a chimeric anti-EGFR monoclonal antibody. European journal of nuclear medicine and molecular imaging. 2007; 34:850-8.
17. Niu G, Li Z, Xie J, Le Q-T, Chen X. PET of EGFR Antibody Distribution in Head and Neck Squamous Cell Carcinoma Models. Journal of Nuclear Medicine. 2009; 50:1116-23.
18. Niu G, Sun X, Cao Q, Courter D, Koong A, Le Q-T, et al. Cetuximab-Based Immunotherapy and Radioimmunotherapy of Head and Neck Squamous Cell Carcinoma. Clinical Cancer Research. 2010; 16:2095-105.
19. Sundaresan G, Yazaki P J, Shively J E, Finn R D, Larson S M, Raubitschek A A, et al. 124I-Labeled Engineered Anti-CEA Minibodies and Diabodies Allow High-Contrast, Antigen-Specific Small-Animal PET Imaging of Xenografts in Athymic Mice. Journal of Nuclear Medicine. 2003; 44:1962-9.
20. Lipovšek D. Adnectins: engineered target-binding protein therapeutics. Protein Engineering Design and Selection. 2011; 24:3-9.
21. Koide A, Gilbreth R N, Esaki K, Tereshko V, Koide S. High-affinity single-domain binding proteins with a binary-code interface. Proceedings of the National Academy of Sciences. 2007; 104:6632-7.
22. Hackel B J, Kimura R H, Gambhir S S. Use of (64)Cu-labeled fibronectin domain with EGFR-overexpressing tumor xenograft: molecular imaging. Radiology. 2012; 263:179-88.
23. Yuan F, Dellian M, Fukumura D, Leunig M, Berk D A, Torchilin V P, et al. Vascular Permeability in a Human Tumor Xenograft: Molecular Size Dependence and Cutoff Size. Cancer Research. 1995; 55:3752-6.
24. Schmidt M M, Wittrup K D. A modeling analysis of the effects of molecular size and binding affinity on tumor targeting. Molecular Cancer Therapeutics. 2009; 8:2861-71.
25. Zahnd C, Kawe M, Stumpp M T, de Pasquale C, Tamaskovic R, Nagy-Davidescu G, et al. Efficient Tumor Targeting with High-Affinity Designed Ankyrin Repeat Proteins: Effects of Affinity and Molecular Size. Cancer Research. 2010; 70:1595-605.
26. Hackel B J, Ackerman M E, Howland S W, Wittrup K D. Stability and CDR composition biases enrich binder functionality landscapes. Journal of molecular biology. 2010; 401:84-96.
27. Koide A, Koide S. Monobodies: antibody mimics based on the scaffold of the fibronectin type III domain. Methods in molecular biology. 2007; 352:95-109.
28. Tolcher A W, Sweeney C J, Papadopoulos K, Patnaik A, Chiorean E G, Mita A C, et al. Phase I and pharmacokinetic study of CT-322 (BMS-844203), a targeted Adnectin inhibitor of VEGFR-2 based on a domain of human fibronectin. Clinical cancer research: an official journal of the American Association for Cancer Research. 2011; 17:363-71.
29. Miao Z, Ren G, Liu H, Jiang L, Cheng Z. Small-Animal PET Imaging of Human Epidermal Growth Factor Receptor Positive Tumor with a 64Cu Labeled Affibody Protein. Bioconjugate chemistry. 2010; 21:947-54.
30. Hackel B J, Kapila A, Wittrup K D. Picomolar affinity fibronectin domains engineered utilizing loop length diversity, recursive mutagenesis, and loop shuffling. Journal of molecular biology. 2008; 381:1238-52.
31. Chappell L L, Dadachova E, Milenic D E, Garmestani K, Wu C, Brechbiel M W. Synthesis, characterization, and evaluation of a novel bifunctional chelating agent for the lead isotopes 203Pb and 212Pb. Nuclear medicine and biology. 2000; 27:93-100.
32. Natarajan A, Gowrishankar G, Nielsen C H, Wang S, Iagaru A, Goris M L, et al. Positron Emission Tomography of (64)Cu-DOTA-Rituximab in a Transgenic Mouse Model Expressing Human CD20 for Clinical Translation to Image NHL. Molecular imaging and biology: MIB: the official publication of the Academy of Molecular Imaging. 2012; 14:608-16.
33. Lu S X, Takach E J, Solomon M, Zhu Q, Law S J, Hsieh F Y. Mass spectral analyses of labile DOTA-NHS and heterogeneity determination of DOTA or DM1 conjugated anti-PSMA antibody for prostate cancer therapy. Journal of pharmaceutical sciences. 2005; 94:788-97.
34. Gong Q, Ou Q, Ye S, Lee W P, Cornelius J, Diehl L, et al. Importance of cellular microenvironment and circulatory dynamics in B cell immunotherapy. Journal of immunology. 2005; 174:817-26.

35. Natarajan A, Habte F, Gambhir S S. Development of a Novel Long-Lived ImmunoPET Tracer for Monitoring Lymphoma Therapy in a Humanized Transgenic Mouse Model. Bioconjugate chemistry. 2012.
36. Loening A M, Gambhir S S. AMIDE: a free software tool for multimodality medical image analysis. Molecular imaging. 2003; 2:131-7.
37. Winiarska M, Glodkowska-Mrowka E, Bil J, Golab J. Molecular mechanisms of the antitumor effects of anti-CD20 antibodies. Frontiers in bioscience: a journal and virtual library. 2011; 16:277-306.
38. Olafsen T, Betting D, Kenanova V E, Salazar F B, Clarke P, Said J, et al. Recombinant anti-CD20 antibody fragments for small-animal PET imaging of B-cell lymphomas. Journal of nuclear medicine: official publication, Society of Nuclear Medicine. 2009; 50:1500-8.
39. Bakir M A, Eccles S, Babich J W, Aftab N, Styles J, Dean C J, et al. c-erbB2 protein overexpression in breast cancer as a target for PET using iodine-124-labeled monoclonal antibodies. Journal of nuclear medicine: official publication, Society of Nuclear Medicine. 1992; 33:2154-60.
40. Jekunen A, Kairemo K, Karnani P. In vivo modulators of antibody kinetics. Acta oncologica. 1996; 35:267-71.
41. Bloom L, Calabro V. FN3: a new protein scaffold reaches the clinic. Drug Discovery Today. 2009; 14:949-55.
42. Pescovitz M D. Rituximab, an anti-cd20 monoclonal antibody: history and mechanism of action. American journal of transplantation: official journal of the American Society of Transplantation and the American Society of Transplant Surgeons. 2006; 6:859-66.
43. Wadas T J, Wong E H, Weisman G R, Anderson C J. Copper chelation chemistry and its role in copper radiopharmaceuticals. Current pharmaceutical design. 2007; 13:3-16.
44. Olafsen T, Sirk S J, Betting D J, Kenanova V E, Bauer K B, Ladno W, et al. ImmunoPET imaging of B-cell lymphoma using 124I-anti-CD20 scFv dimers (diabodies). Protein engineering, design & selection: PEDS. 2010; 23:243-9.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

Sequences:

SEQ ID NO: 1
GG<u>YNCEPANPSEKNSPSTQYCYS</u> chemically synthesized extracellular peptide loop (aa 165-185) of CD20 antigen (FN3$_{CD20}$, also called FN3)
SEQ ID NO: 2
ASVSDVPRDLEVVAATPTSLLISW<u>CRQRCADS</u>YRITYGETGGNSPVQEF TVP<u>GSWKT</u>ATISGLKPGVDYTITVYVVT<u>HYYGWDRYSH</u>PISINYRTGSH

HHHHH.

chemically synthesized FN3 probe sequence with affinity for the extracellular peptide loop (amino acid 165 to 185) of the human CD20 domain.

(FN3$_{wt}$)
SEQ ID NO: 3
VSDVPRDLEVVAATPTSLLISW<u>DAPAVTVRY</u>YRITYGETGGNSPVQEFT

VP<u>GSKST</u>ATISGLKPGVDYTITVYAVT<u>GRGDSPASSK</u>PISINYRT chemically synthesized fragment of human fibronectin type 3 (FN3) domain (FN3$_{CD20-01}$)
SEQ ID NO: 4
ASVSDVPRDLEVVAATPTSLLISW<u>HYTCAGS</u>YRITYGETGGNSPVQEFT VP<u>GSWKT</u>ATISGLKPGVDYTITVYAVT<u>HYYGWDRYSH</u>PISINYRTGSHH

HHHH chemically synthesized FN3 probe sequence that may have affinity for the extracellular peptide loop (amino acid 165 to 185) of the human CD20 domain.

(FN3$_{CD20-02}$)
SEQ ID NO: 5
ASVSDVPRDLEVVAATPTSLLISW<u>HYTCADS</u>YRITYGETGGNSPVQEFT

VP<u>WYVSN</u>ATISGLKPGVDYTITVYVVT<u>HYYGWDRYSH</u>PISINYRTGSHH

HHHH chemically synthesized FN3 probe sequence that may have affinity for the extracellular peptide loop (amino acid 165 to 185) of the human CD20 domain.

(FN3$_{CD20-03}$)
SEQ ID NO: 6
ASVSDVPRDLGVVAATPTSLLISW<u>HSSDVS</u>YYRITYGETGGNSPVQEFT

VP<u>YWFTNT</u>TISGLKPGVDYTITVYAAT<u>YRDCSSE</u>PISINYRTGSHHHHH

H chemically synthesized FN3 probe sequence that may have affinity for the extracellular peptide loop (amino acid 165 to 185) of the human CD20 domain.

The first, second, and third underlined portions in each of SEQ ID NOs: 2-6 represent the diversified BC, DE, and FG loops, respectively, for each variant, which are illustrated in FIG. 1A.

We claim at least the following:

1. A method of diagnosing the presence of a non-Hodgkin's lymphoma in a subject, the method comprising:
    administering to the subject a labeled probe with a sequence having SEQ. ID. NO.: 2 or SEQ. ID. NO.: 4, wherein the probe binds to a CD20 protein;
    imaging at least a portion of the subject; and
    detecting the labeled probe, wherein the location of the labeled probe corresponds to the location of the non-Hodgkin's lymphoma.

2. The method of claim 1, wherein the labeled probe includes a metal selected from the group consisting of: $^{64}$Cu, $^{89}$Zr, $^{86}$Y and $^{68}$Ga, and is conjugated with the sequence.

3. The method of claim 2, wherein the metal is conjugated to the sequence via a lysine amino acid or a N-terminus free amine site.

4. The method of claim 2, wherein at least two metals are conjugated to the sequence.

5. The method of claim 2, wherein the metal is conjugated to the sequence using a chelator selected from the group consisting of: DOTA, NOTA, EDTA, desferrioxamine (Df), DTPA, and TETA.

6. The method of claim 5, wherein the metal is $^{64}$Cu and the chelator is DOTA.

7. The method of claim 1, wherein the metal is $^{64}$Cu and is conjugated to the sequence via a lysine amino acid or a N-terminus free amine site.

8. A method of monitoring the progress of a non-Hodgkin's lymphoma in a subject, the method comprising:
    administering to the subject a labeled probe with a sequence having SEQ. ID. NO.: 2 or SEQ. ID. NO.: 4, wherein the probe binds to a CD20 protein;
    imaging at least a portion of the subject; and
    detecting the labeled probe, wherein location of the labeled probe corresponds to the location of the non-Hodgkin's lymphoma, wherein the location is monitored.

9. The method of claim 8, further comprising repeating the steps of claim 8 to monitor the location corresponding to the non-Hodgkin's lymphoma.

10. The method of claim 8, wherein the labeled probe includes a metal selected from the group consisting of: $^{64}$Cu, $^{89}$Zr, $^{86}$Y and $^{68}$Ga, and is conjugated with the sequence.

11. The method of claim 10, wherein the metal is conjugated to the sequence via a lysine amino acid or a N-terminus free amine site.

12. The method of claim 10, wherein at least two metals are conjugated to the sequence.

13. The method of claim 10, wherein the metal is conjugated to the sequence using a chelator selected from the group consisting of: DOTA, NOTA, EDTA, Df, DTPA, and TETA.

14. The method of claim 13, wherein the metal is $^{64}$Cu and the chelator is DOTA.

15. The method of claim 10, wherein the metal is $^{64}$Cu and is conjugated to the sequence via a lysine amino acid or a N-terminus free amine site.

16. The method of claim 1, wherein the sequence is SEQ. ID. NO.: 2.

17. The method of claim 1, wherein the sequence is SEQ. ID. NO.: 4.

18. The method of claim 8, wherein the sequence is SEQ. ID. NO.: 2.

19. The method of claim 8, wherein the sequence is SEQ. ID. NO.: 4.

* * * * *

SEQUENCE LISTING

<160> NUMBER OF SEQ ID NOS: 6

<210> SEQ ID NO 1
<211> LENGTH: 23
<212> TYPE: PRT
<213> ORGANISM: Artificial Sequence
<220> FEATURE:
<223> OTHER INFORMATION: chemically synthesized extracellular peptide
      loop (aa 165-185) of CD20 antigen

<400> SEQUENCE: 1

Gly Gly Tyr Asn Cys Glu Pro Ala Asn Pro Ser Glu Lys Asn Ser Pro
1               5                   10                  15

Ser Thr Gln Tyr Cys Tyr Ser
            20

<210> SEQ ID NO 2
<211> LENGTH: 103
<212> TYPE: PRT
<213> ORGANISM: Artificial Sequence
<220> FEATURE:
<223> OTHER INFORMATION: chemically synthesized FN3 probe sequence with
      affinity for the extracellular peptide loop (amino acid 165 to
      185) of the human CD20 domain.

<400> SEQUENCE: 2

Ala Ser Val Ser Asp Val Pro Arg Asp Leu Glu Val Val Ala Ala Thr
1               5                   10                  15

Pro Thr Ser Leu Leu Ile Ser Trp Cys Arg Gln Arg Cys Ala Asp Ser
            20                  25                  30

Tyr Arg Ile Thr Tyr Gly Glu Thr Gly Gly Asn Ser Pro Val Gln Glu
        35                  40                  45

Phe Thr Val Pro Gly Ser Trp Lys Thr Ala Thr Ile Ser Gly Leu Lys
    50                  55                  60

Pro Gly Val Asp Tyr Thr Ile Thr Val Tyr Val Val Thr His Tyr Tyr
65                  70                  75                  80

Gly Trp Asp Arg Tyr Ser His Pro Ile Ser Ile Asn Tyr Arg Thr Gly
                85                  90                  95

Ser His His His His His His
            100

<210> SEQ ID NO 3
<211> LENGTH: 94
<212> TYPE: PRT
<213> ORGANISM: Artificial Sequence
<220> FEATURE:
<223> OTHER INFORMATION: chemically synthesized fragment of human
      fibronectin type 3 (FN3) domain.

<400> SEQUENCE: 3

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr

```
                85                  90

<210> SEQ ID NO 4
<211> LENGTH: 102
<212> TYPE: PRT
<213> ORGANISM: Artificial Sequence
<220> FEATURE:
<223> OTHER INFORMATION: chemically synthesized FN3 probe sequence that
      may have affinity for the extracellular peptide loop (amino acid
      165 to 185) of the human CD20 domain

<400> SEQUENCE: 4

Ala Ser Val Ser Asp Val Pro Arg Asp Leu Glu Val Val Ala Ala Thr
1               5                   10                  15

Pro Thr Ser Leu Leu Ile Ser Trp His Tyr Thr Cys Ala Gly Ser Tyr
            20                  25                  30

Arg Ile Thr Tyr Gly Glu Thr Gly Gly Asn Ser Pro Val Gln Glu Phe
        35                  40                  45

Thr Val Pro Gly Ser Trp Lys Thr Ala Thr Ile Ser Gly Leu Lys Pro
    50                  55                  60

Gly Val Asp Tyr Thr Ile Thr Val Tyr Ala Val Thr His Tyr Tyr Gly
65                  70                  75                  80

Trp Asp Arg Tyr Ser His Pro Ile Ser Ile Asn Tyr Arg Thr Gly Ser
                85                  90                  95

His His His His His His
            100

<210> SEQ ID NO 5
<211> LENGTH: 102
<212> TYPE: PRT
<213> ORGANISM: Artificial Sequence
<220> FEATURE:
<223> OTHER INFORMATION: chemically synthesized FN3 probe sequence that
      may have affinity for the extracellular peptide loop (amino acid
      165 to 185) of the human CD20 domain

<400> SEQUENCE: 5

Ala Ser Val Ser Asp Val Pro Arg Asp Leu Glu Val Val Ala Ala Thr
1               5                   10                  15

Pro Thr Ser Leu Leu Ile Ser Trp His Tyr Thr Cys Ala Asp Ser Tyr
            20                  25                  30

Arg Ile Thr Tyr Gly Glu Thr Gly Gly Asn Ser Pro Val Gln Glu Phe
        35                  40                  45

Thr Val Pro Trp Tyr Val Ser Asn Ala Thr Ile Ser Gly Leu Lys Pro
    50                  55                  60

Gly Val Asp Tyr Thr Ile Thr Val Tyr Val Val Thr His Tyr Tyr Gly
65                  70                  75                  80

Trp Asp Arg Tyr Ser His Pro Ile Ser Ile Asn Tyr Arg Thr Gly Ser
                85                  90                  95

His His His His His His
            100

<210> SEQ ID NO 6
<211> LENGTH: 99
<212> TYPE: PRT
<213> ORGANISM: Artificial Sequence
<220> FEATURE:
<223> OTHER INFORMATION: chemically synthesized FN3 probe sequence that
      may have affinity for the extracellular peptide loop (amino acid
      165 to 185) of the human CD20 domain

<400> SEQUENCE: 6
```

```
Ala Ser Val Ser Asp Val Pro Arg Asp Leu Gly Val Val Ala Ala Thr
1               5                   10                  15

Pro Thr Ser Leu Leu Ile Ser Trp His Ser Ser Asp Val Ser Tyr Tyr
            20              25                  30

Arg Ile Thr Tyr Gly Glu Thr Gly Gly Asn Ser Pro Val Gln Glu Phe
        35              40                  45

Thr Val Pro Tyr Trp Phe Thr Asn Thr Thr Ile Ser Gly Leu Lys Pro
    50              55                  60

Gly Val Asp Tyr Thr Ile Thr Val Tyr Ala Ala Thr Tyr Arg Asp Cys
65              70              75                      80

Ser Ser Glu Pro Ile Ser Ile Asn Tyr Arg Thr Gly Ser His His His
                85                  90                  95

His His His
```